United States Patent
Haenel

(10) Patent No.: US 6,268,595 B1
(45) Date of Patent: Jul. 31, 2001

(54) CIRCULATION WARMER

(76) Inventor: Jon Haenel, 340 Sugartop Rd., White River Junction, VT (US) 05001-9224

(*) Notice: Subject to any disclaimer, the term of this patent is extended or adjusted under 35 U.S.C. 154(b) by 0 days.

(21) Appl. No.: 09/511,595
(22) Filed: Feb. 23, 2000
(51) Int. Cl.[7] .................................................. H05B 3/34
(52) U.S. Cl. .......................................... 219/528; 219/211
(58) Field of Search ..................................... 219/200, 211, 219/212, 217, 527, 528, 529, 549; 602/2, 41, 54, 96; 128/888, 889; 607/96, 99, 103, 111; 604/113, 114

(56) References Cited

U.S. PATENT DOCUMENTS

| | | | |
|---|---|---|---|
| 3,569,666 | 3/1971 | Murphy et al. | 219/211 |
| 3,895,638 | 7/1975 | Ito | 128/379 |
| 4,303,074 | * 12/1981 | Bender | 219/211 |
| 4,535,482 | 8/1985 | Spector et al. | 2/160 |
| 4,587,672 | 5/1986 | Madnick et al. | 2/158 |
| 4,759,084 | 7/1988 | Madnick et al. | 2/158 |
| 4,950,868 | 8/1990 | Moss et al. | 219/211 |
| 5,035,003 | 7/1991 | Rinehart | 2/159 |
| 5,072,875 | 12/1991 | Zacoi | 128/400 |
| 5,160,828 | 11/1992 | Olsen | 219/211 |
| 5,250,032 | 10/1993 | Carter, Jr. et al. | 604/113 |
| 5,509,143 | 4/1996 | Yates et al. | 2/160 |
| 5,531,775 | 7/1996 | Sasaki et al. | 607/96 |
| 5,541,388 | 7/1996 | Gadd | 219/211 |
| 5,620,621 | 4/1997 | Sontag | 219/211 |
| 6,113,561 | * 9/2000 | Augustine | 602/2 |

* cited by examiner

Primary Examiner—Tu Ba Hoang

(57) ABSTRACT

An apparatus and method for warming blood of a user prior to distribution to an extremity of a user includes a source of energy suitable for distribution as heat. A transfer path connects the source of energy to a vascular distribution system including a contact pad. The contact pad is configured to conduct the distributed heat through a user's skin and into the user's bloodstream at a vascular surface location defined as a spot where a major blood vessel or vessels larger than capillaries pass sufficiently near the skin surface that heat may be conducted directly from the surface of the skin into the blood flowing through the major blood vessel or vessels toward a body extremity. A positioner connects to the contact pad and secures the contact pad in intimate and complete contact with the vascular surface location. The positioner is preferably shaped and sized to conform to the body region near the vascular surface location and effective to maintain substantially complete contact between the contact pad and the skin of a user.

20 Claims, 11 Drawing Sheets

CIRCULATION WARMER

BACKGROUND

1. Related Applications

This application claims priority to U.S. Provisional Application, Ser. No. 60/121,191, filed on Feb. 23, 1999 and directed to a CIRCULATION WARMER.

2. The Field of the Invention

This invention relates to the field of cold weather gear, and, more particularly, to novel systems and methods for maintaining the warmth, tactile sense, and dexterity of body extremities in a cold environment while leaving the body extremities substantially uncovered.

3. The Background Art

A variety of devices for warming body extremities have been developed by those skilled in the art. Examples of these devices are gloves or mittens for warming hands and fingers, socks for warming feet and toes, and various garments for warming the head and face. These prior art garments are typically formed of cloth comprising natural and/or synthetic fibers or leather. These garments typically operate by substantially covering the body extremity to be warmed thereby capturing the natural heat generated by the body extremity and maintaining the captured heat proximate to the body extremity.

A significant disadvantage of the garments that rely solely on the natural heat generated by the affected body extremity of the type generally described above includes the inability of such garments to maintain the affected body extremity sufficiently warm under extremely cold conditions. To address the aforementioned disadvantage, heated garments include artificial heat sources or heating elements for providing additional heat to maintain the body extremity acceptably warm. Such heated garments (e.g. heated socks, heated gloves, or the like) typically include heating elements that provide heat directly on or around the tissue of the affected body extremity (e.g., hands, fingers, feet, toes, and the like). The heating elements in such prior art devices typically extend substantially throughout the body of the garment. For example, the heating elements in heated gloves of the prior art typically extend substantially throughout the glove body across the palm area and up through the finger arcs. Various types of heating elements have been incorporated into the heated garments, using electrical resistance, slowly combustible materials, and/or chemical reactions to produce heat.

Although seemingly useful for their intended purposes, several practical disadvantages inure to both unheated and heated garments. For example, in the case of heated garments, the extension of heating elements substantially throughout the bodies of such garments often results in provision of more heat than is required thereby causing overheating of the affected body extremity. Especially in the case of heated garments that rely on electrical resistance as a heat source, the extension of the heating element substantially throughout the body of the garment results in rapid depletion of the power source (e.g., typically batteries or other rechargeable source of electricity).

Many forms of work and recreation that require dexterity and tactile sense in the hands and fingers are conducted under cold environmental conditions (e.g., farm work, construction, equipment repair, skiing, hunting, and the like). Another significant disadvantage of heated gloves in particular includes placement of the heating elements throughout the palm and finger areas thereby impeding dexterity and tactile sense in the hand and fingers, which interferes with the work or recreation being conducted by the wearer. The placement of the heating elements throughout the palm and finger areas of heated gloves also causes rapid degradation of the heating elements due to stress and strain caused by bending of the hand and fingers and gripping of objects (e.g., ski poles, tools, equipment, and the like).

Both heated and unheated garments often include excessive amounts of insulation material distributed throughout the bodies of such garments resulting in oversized, cumbersome garments that impede the dexterity and tactile sense of the body extremity with which such garments are used. In an effort to address the problems caused by loss of dexterity and tactile sense in the hands and fingers, devices comprising fingerless gloves having a mitten top can be used to cover, and thus warm, the fingers of the wearer or that can be folded back when increased dexterity and tactile sense in the fingers is desirable. Such fingerless gloves may or may not include an artificial heat source to enhance the warming of the hands and fingers. A significant disadvantage of such fingerless gloves includes the rapid loss of dexterity and tactile sense in the fingers upon folding back the mitten top and exposing the fingers to the cold environmental conditions.

While unheated garments for covering and warming body extremities, as well as artificially heated garments for covering and warming body extremities appear generally suitable for their intended purposes, these garments nevertheless leave much to be desired from the standpoint of effectiveness of operation, functionality as to universal application, simplicity of construction in relation to the extension of heating elements substantially throughout the body of such garments and relatively complex structure, and manufacturing costs. As will be appreciated in this particular art, economic considerations are significant when dealing with the highly competitive garment industry. Relatively complicated devices are frequently found to be commercially impractical. Accordingly, even a slight savings in cost may substantially enhance the commercial appeal of a particular component or assembly when considering issues of mass production of the product.

In accordance therewith, it would be desirable to provide an improved device for warming body extremities that realizes the many advantages of the prior art devices while at the same time eliminating the disadvantages associated therewith. Such an apparatus for warming body extremities under cold environmental conditions without substantially degrading the dexterity and tactile sense of the body extremity is disclosed and claimed herein.

BRIEF SUMMARY AND OBJECTS OF THE INVENTION

In view of the foregoing, it is a primary object of the present invention to provide a circulation warmer for warming a body extremity while allowing the body extremity to be uncovered or sparsely covered so that dexterity and tactile sense in the body extremity are maximized.

It is further an object of the invention to provide a circulation warmer that requires no moving parts or parts that are required to flex or bend excessively.

It is also an object of the invention to provide a circulation warmer that is simple and economical to manufacture.

Similarly, it is an object of the invention to provide a circulation warmer that is simple to maintain and use.

Moreover, it is an object of the invention to provide a circulation warmer that minimizes the use of specialized parts in its manufacture (i.e. the warmer may be manufactured with off-the-shelf components).

Further, it is an object of the invention to provide a circulation warmer that functions for extended periods of time before extinguishing and therefore requiring replacement of a replenishable fuel source (e.g., batteries, rechargeable batteries, fuel sticks, chemicals, or the like).

Consistent with the foregoing objects, and in accordance with the invention as embodied and broadly described herein, a method and apparatus are disclosed in one embodiment of the present invention as including an apparatus and method for warming blood of a user prior to distribution to an extremity of a user. The apparatus may include a source of energy suitable for distribution as heat. A transfer path preferably connects the source of energy to a vascular distribution system including a contact pad.

The contact pad may be configured to conduct the distributed heat through a user's skin and into the user's bloodstream at a vascular surface location, defined as a spot where a major blood vessel or vessels larger than capillaries pass sufficiently near the skin surface, substantially uncovered by muscle or tissue mass so that heat may be conducted directly from the surface of the skin into the blood flowing through the major blood vessel or vessels toward a body extremity.

A positioner may be connected to the contact pad and may secure the contact pad in intimate and complete contact with a vascular surface location. The positioner is preferably shaped and sized to conform to the body region near the vascular surface location and effective to maintain substantially complete contact between the contact pad and the skin of a user.

The apparatus may also include a controller configured to control the distribution of heat to the contact pad. The distribution of energy may also include conversion from one mode of energy to another, such as the conversion from electricity to heat energy. The apparatus may also include an exchanger for exchanging energy from one medium to a different medium.

The transfer path of the apparatus may be a line. Such a line may be an electrical line, a fluid line, a heat transfer line, or other type of line. The contact pad may be a vascular contact pad, specifically designed to conduct heat through a user's skin and into the user's bloodstream via a subcutaneous vessel. The vascular contact pad may further be a fluid conduit configured to convect heat from a working fluid to a contact surface, such as a user's skin.

A method in accordance with the invention may include the steps of placing a contact pad against a vascular surface location of a user to be in thermally conducting relation thereto, connecting the contact pad to a source of energy, transferring energy from the source of energy toward the contact pad, providing energy as heat through the contact pad, conducting heat from a contact surface of the contact pad to the skin of a user; and conducting heat from the skin of a user into the bloodstream of a user. The method may also include the step of securing the contact pad with a positioner to a location on a user's body. In the method, the positioner may be shaped and sized to conform to the body region proximate the vascular surface location. The positioner may be made of a flexible material for providing comfortable fit to a user. The flexible material may be a material suitable for snugging the contact pad into complete contact with the vascular surface location.

The method may also include the actual delivery of energy to the contact pad. The energy employed in the method may be electric current, a heated fluid or the like. The method may also include the step of controlling the transfer of energy toward the contact pad.

An alternate method for warming blood of a user prior to entry into a body extremity may include providing a source of energy suitable for distribution as heat, providing a contact pad configured to conduct heat to the skin of a user, providing a positioner attached to the contact pad for securing the contact pad in intimate contact with a vascular surface location wherein the positioner is shaped and sized to conform to the body region proximate the vascular surface location and is effective to maintain substantially complete contact between the contact pad and the skin of a user, providing a transfer path connecting the source to the contact pad, and transferring energy from the source toward the contact pad.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

DETAILED DESCRIPTION OF THE PREFERRED EMBODIMENTS

It will be readily understood that the components of the present invention, as generally described and illustrated in the Figures herein, could be arranged and designed in a wide variety of different configurations. Thus, the following more detailed description of the embodiments of the system and method of the present invention, as represented in FIGS. 1 through 19, is not intended to limit the scope of the invention, as claimed, but is merely representative of the presently preferred embodiments of the invention.

The presently preferred embodiments of the invention will be best understood by reference to the drawings, wherein like parts are designated by like numerals throughout. FIGS. 1–19 illustrate certain presently preferred embodiments of apparatus and methods in accordance with the invention. Those of ordinary skill in the art will, of course, appreciate that various modifications to the detailed schematic diagrams may easily be made without departing from the essential characteristics of the invention, as described. Thus, the following description of the Figures is intended only by way of example, and simply illustrates certain presently preferred embodiments of the invention as claimed herein.

Figure 1:
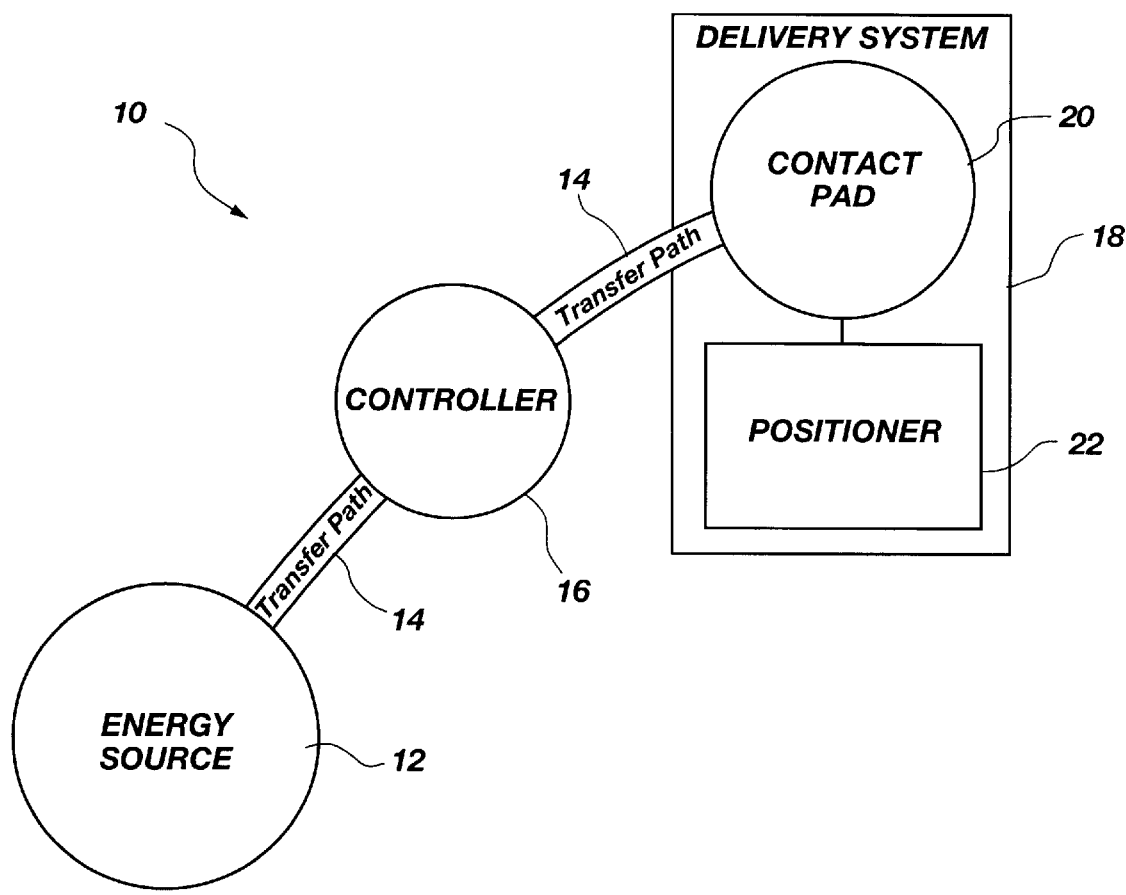
FIG. 1 is a schematic block diagram illustrating one embodiment of an apparatus for warming the blood of a user prior to distribution to an extremity of a user in accordance with the invention.
Figure 2:
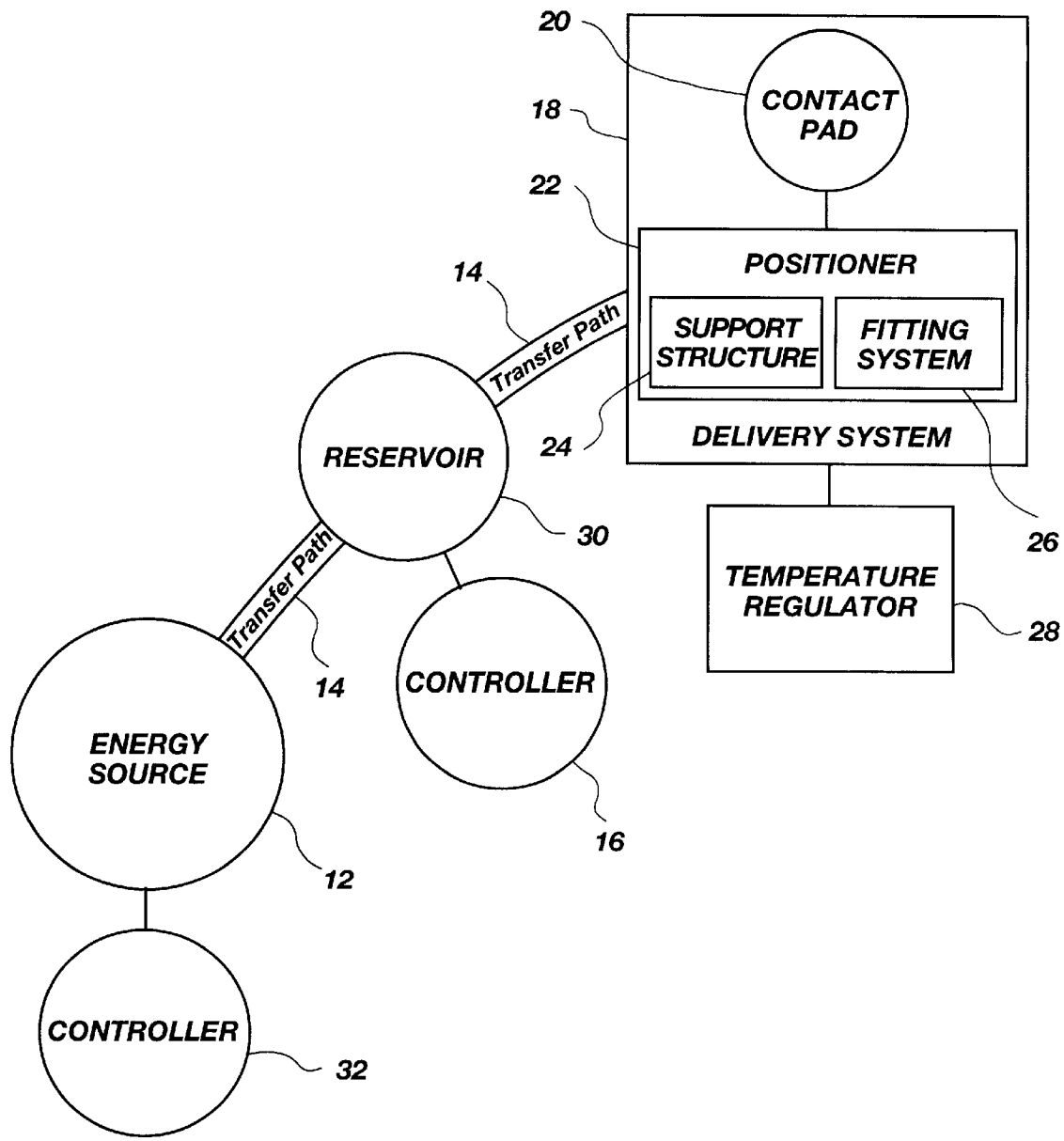
FIG. 2 is a schematic block diagram illustrating optional features of the embodiment of FIG. 1 in accordance with the invention.

Referring to FIGS. 1–19, generally, and specifically to FIGS. 1–2, an apparatus 10 may be referred to as a circulation warmer 10 or a circulatory heater 10. Referring to FIG. 1, the apparatus 10 may include an energy source 12, a transfer path 14, a controller 16 and a vascular delivery system 18. The vascular delivery system 18 may further include a contact pad 20 and a positioner 22.

An energy source 12 may be any source of energy suitable for conversion to heat or suitable for distribution as heat. For example, suitable energy sources 12 may include electric batteries, AC or DC electric current, thermoelectric converters, fuel cells, solar photovoltaic cells, body heat from a user's body core, chemical reactions, low temperature combustion of materials, solar thermal energy or the like. Energy may also be transmitted from an energy source 12 and stored in heat retaining materials such as solids, liquids, gels, and the like, for later use.

Typically, the transfer path 14 connects the energy source 12 to the vascular delivery system 18. The transfer path 14 most commonly connects directly to the contact pad 20 of the vascular delivery system 18. The transfer path 14 typically functions to transfer energy or heat from the energy source 12 to the contact pad 20 for delivery. A suitable transfer path 14 may correspond to the particular type of energy source 12 being used in a warmer 10. For example, a circulation warmer 10 employing electrical energy typically includes transfer paths 14 that are wires suitable for transfer of electricity. Other effective transfer paths 14, depending on the form of the energy source 12 employed, may include tubes suitable for transfer of heated fluids or heated gases, conduction of heat energy from an energy source 12 through a user's skin, radio frequencies corresponding to a receiver on a contact pad 20, conduction of heat energy through an insulating material and the like.

A controller 16 may operate in cooperation with the transfer path 14 to maintain the operating temperatures of the contact pad 20 of the vascular delivery system 18 within a range that is safe, effective and comfortable for a user. A controller 16 may comprise any suitable regulator effective to regulate the transfer of energy from the energy source 12 to the contact pad 20, a contact temperature or both. For example, in a circulation warmer 10 that employs electrical energy, a suitable controller 16 may be a voltage or amperage regulator. In a circulation warmer 10 that employs heated fluid the controller 16 may comprise a flow control for controlling the flow of heated fluid through the transfer path 14 through the vascular delivery system 18. Thermostatic controls 16 may regulate temperatures.

As shown in FIG. 1, the contact pad 20 of the vascular delivery system 18 is typically configured to conduct heat through the skin and into the bloodstream of a user. The bloodstream in the body of a warm-blooded animal, such as a human being, is the flow in comparatively larger blood vessels that feeds into a network of smaller vessels for eventual capillary distribution into bulk tissues of the body. Bulk tissues of the body include muscle mass, fats, organs of the body and the like.

The contact pad 20 may comprise any heat-generating or heat-storing device, medium, means, or delivery system suitable for conducting heat through the skin of a user. Suitable contact pads 20 include without limitation electrical resistance heaters, combustion chambers or pouches configured to contain low temperature combustibles materials, chambers or pouches configured for circulation of heated fluid therethrough, chambers or pouches configured to contain low temperature heat retaining solids, liquids or gels, chambers or pouches configured to contain comparatively low temperature (i.e. insulated to within 10–20 degrees Fahrenheit of the body) heat-producing chemical reactions and the like.

The positioner 22 of the vascular delivery system 18 is typically connected to the contact pad 20 and functions to emplace the contact pad 20 over a selected region of the body of a user. The positioner 22 also functions to maintain the contact pad 20 in intimate and complete contact with the skin of a user. As shown in FIG. 2, the positioner 22 may further comprise a support structure 24 and a fitting system 26. The support structure 24 is typically connected directly to and supports the contact pad 20. The support structure 24 is typically formed for use with a specific portion of a user's body. For example, a suitable support structure 24 may be a glove, a sock, or other item formed for use at or near a specific location on the body of a user. The fitting system 26 typically functions to adjust the size, shape, or contour of the support structure 24 to bring the contact pad 20 into complete contact with the skin of a user. For example, the fitting system 26 may comprise an adjustable length securing strap, an elastic band or the like.

As depicted in FIG. 2, a circulation warmer 10 may additionally or alternatively include a temperature regulator 28, a reservoir 30 and a controller 32. A temperature regulator 28 may be connected directly to the vascular delivery system 18 to regulate the amount and/or intensity of heat delivered by the contact pad 20 through the skin of a user. The temperature regulator 28 may enable a user to select the quantity and intensity of heat to be transferred from the contact pad 20 through the skin and into the bloodstream of a user.

The reservoir 30 is typically employed in a fluid-based circulation warmer 10. The reservoir 30 functions to store fluid near the body core of a user for conduction of the core body heat of the user into the fluid contained in the reservoir 30. A controller 16 may be used in connection with a reservoir 30 to regulate the flow of fluid into the reservoir 30 for storage and heating and flow of fluid out of the reservoir 30 for transfer through the transfer path 14 to the vascular delivery system 18.

A controller 32 may be connected directly to the energy source 12 for controlling the use and/or transfer of energy produced or stored by the energy source 12. For example, a circulation warmer 10 based on electrical power may include a controller 32 constituting a voltage regulator, current limiter, or thermostat that operates in connection with the energy source 12 (e.g. batteries or other source of electrical energy) to regulate the flow of electrical power from the energy source 12 through the transfer path 14 to the contact pad 20.

Figure 3:
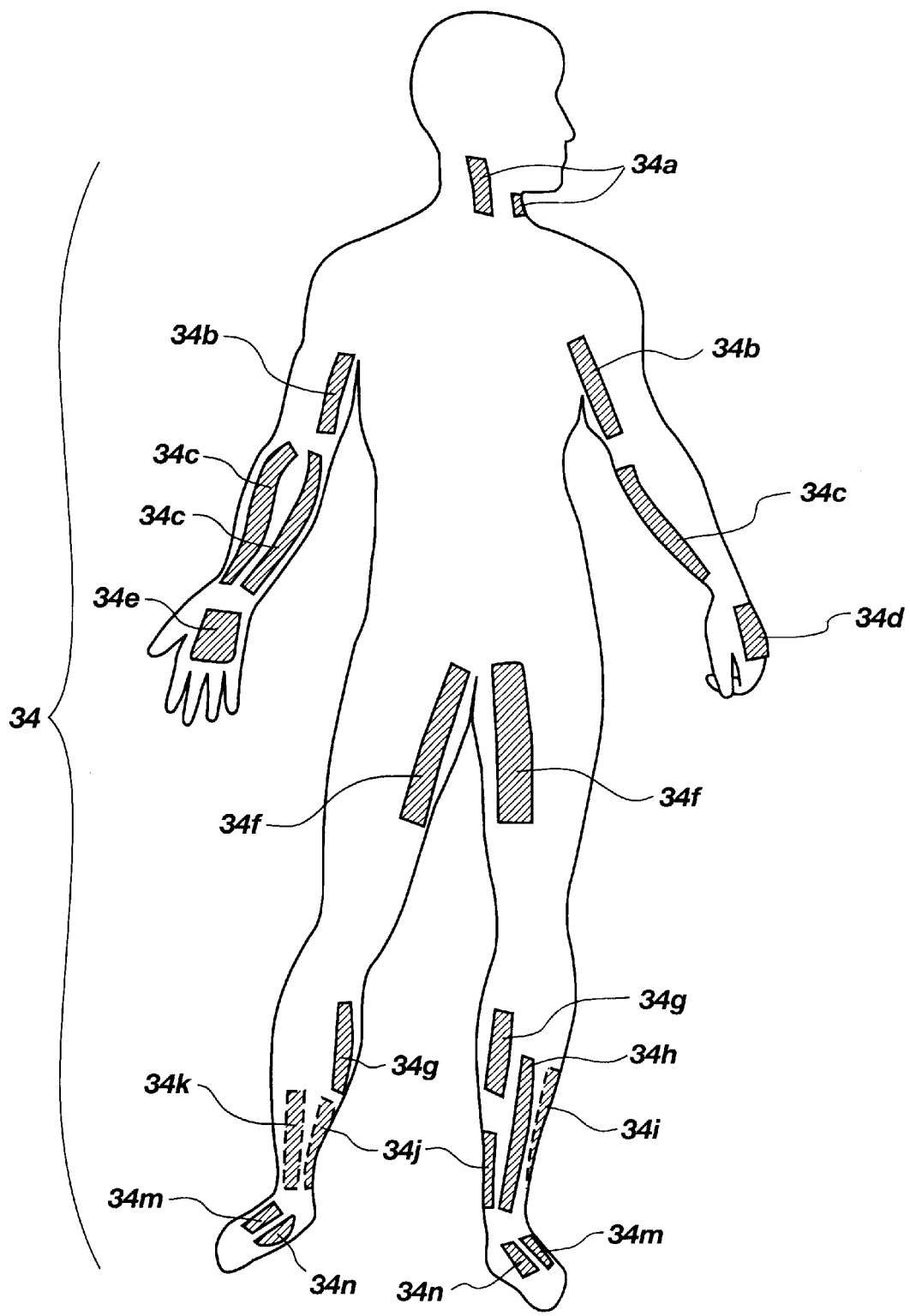
FIG. 3 is a perspective view illustrating suitable vascular surface locations on the human body in accordance with the invention.

Referring to FIG. 3, the human body includes a variety of vascular surface locations 34 (e.g. specific examples being locations 34a–n), defined as areas of the body where a major blood vessel or vessels substantially larger (over an order of magnitude larger) than capillaries pass sufficiently near the skin surface that heat may be conducted directly from the surface of the skin into the blood flowing through the major blood vessel or vessels with the heat passing substantially solely through the skin, the vessel wall, and any intermediate connecting or minor fatty tissue. Vascular surface locations 34 are characteristically exemplified by an absence of significant muscle mass or insulating fat tissue mass that may absorb and/or dissipate the flow of heat to blood in the bloodstream, or significant muscle thickness or other tissue that may resist and/or impede the conduction of heat into blood in the bloodstream.

As shown in FIG. 3, the vascular surface locations 34 of the human body are located along the arteries leading from the body core to body extremities. The heating of blood at one or more of the vascular surface locations 34a–n as the blood flows from the body core past a selected vascular surface location 34 to a selected body extremity (e.g., hand, finger, foot, toe, head, face, nose, or the like) increases the quantity of heat delivered to the selected extremity by the blood flowing to the extremity.

The vascular delivery system 18 is preferably sized and shaped to be comfortably disposed at or over one of the vascular surface locations 34a–n on the body of a user to enable the conduction of heat from the contact pad 20 into the blood in the bloodstream. The contact pad 20 may be connected to a positioner 22, typically including a support system 24 and fitting system 26. Preferably, the positioner 22 is configured to secure the contact pad 20 into intimate and complete contact with one of the vascular surface locations 34a–n of the body of a user. The positioner 22 is preferably sized and shaped such that the engagement between the contact pad 20 and one of the vascular surface locations 34a–n is comfortable for a user.

The apparatus 10 warms blood flowing through the arteries to a body extremity of a user. Especially in extremely cold environmental conditions, blood cools as it travels through the arteries away from the body core to the extremities of the body degrading the body's ability to maintain the temperature of body extremities within the acceptable range. Heat may be conducted from a contact pad 20 through the skin of a user and into blood flowing through the bloodstream to a body extremity of a user. Since arteries carry blood away from the heart and toward body extremities, arteries are usually the designated thermal carriers for the heat transferred from the contact pad 20 and into the bloodstream. Nevertheless, veins or other blood vessels may be relied upon as appropriate.

The heating of the blood traveling through the bloodstream of a user toward a body extremity also causes vasodilation (i.e. increase in diameter) of the arteries leading to the body extremity and vasodilation of the veins leading away from the body extremity thereby resulting in increased blood flow through the body extremity and a corresponding increase in heat transfer to the tissue constituting the body extremity. A small amount of heat is also transferred by conduction through the skin from the location where the contact pad 20 is secured over a selected vascular surface location 34 of a user to a nearby body extremity. The presently preferred embodiments of the present invention are designed for use by a human user, but the present invention may be adapted for use by or with any warm-blooded animal.

The scope of the invention is as broad as generally described above. The illustrations contained in FIGS. 4–19 are merely representative of certain, presently preferred embodiments of the invention and should not be interpreted to be limiting of the scope of the invention broadly described above. Those presently preferred embodiments of the invention will be best understood by reference to FIGS. 4–19.

Figure 4:
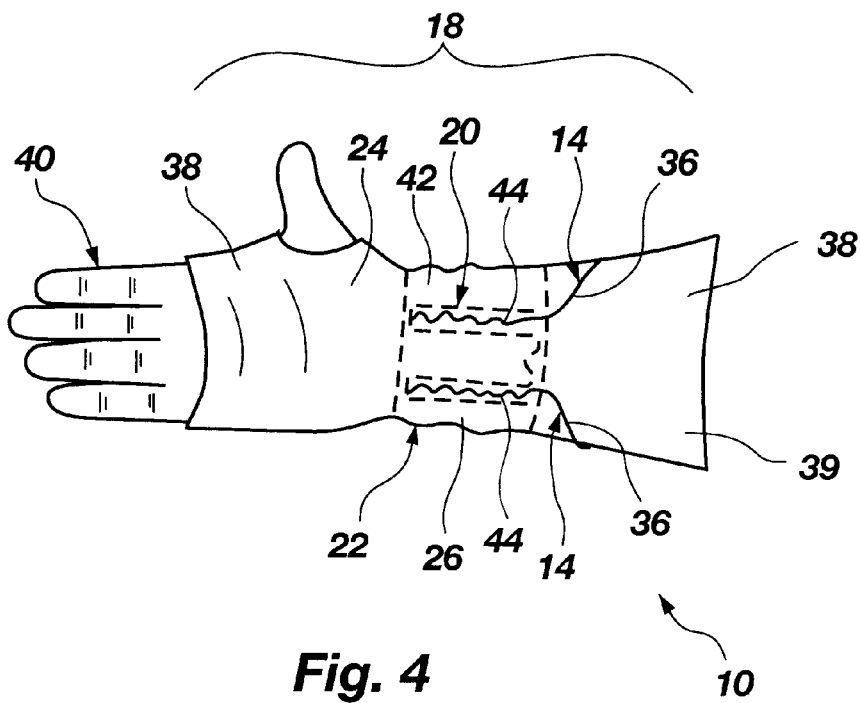
FIG. 4 is an anterior perspective view of one embodiment of a circulation warmer in accordance with the invention.
Figure 5:
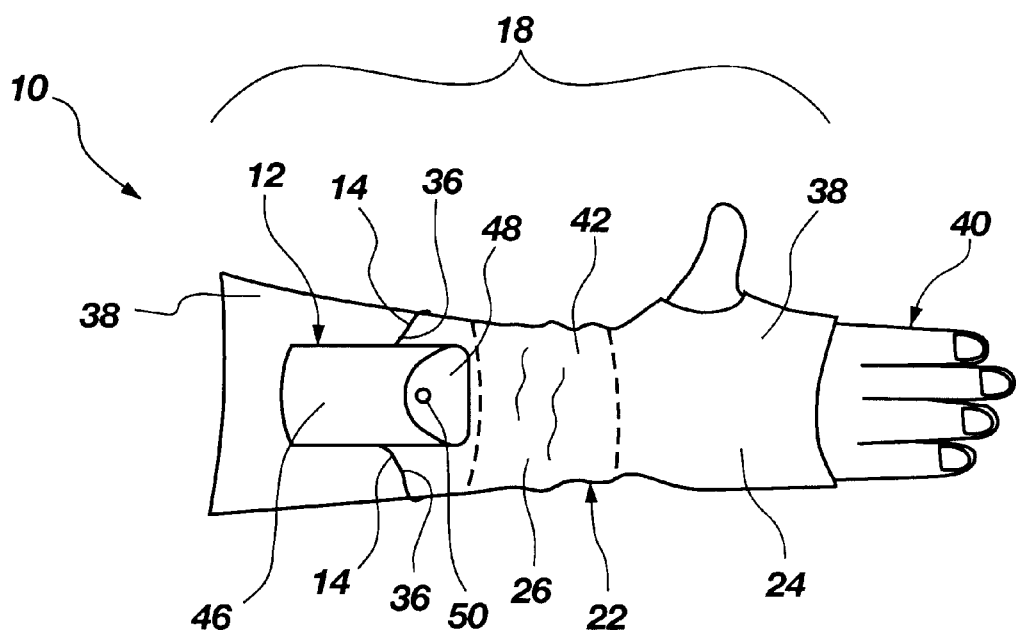
FIG. 5 is a posterior perspective view of the embodiment of the circulation warmer of FIG. 4.

Referring to FIGS. 4–5, in one presently preferred embodiment a circulation warmer 10 comprises an energy source 12, transfer path 14 away therefrom and back, and a vascular delivery system 18 for use near the hand 40 of a user. The vascular delivery system 18 further comprises contact pads 20 and a positioner 22 further comprising a support structure 24 and a fitting system 26. In the depicted embodiment, the energy source 12 comprises one or more batteries (not shown) for storing and providing electrical energy, the transfer paths 14 comprise electrical wires 36, and the contact pads 20 comprise electrical resistance heaters 44. The batteries supply electricity via the electrical wires 36 for delivering electricity to the electrical resistance heaters 44, which produce heat as electricity passes therethrough.

In the depicted embodiment, the positioner 22 of the vascular delivery system 18 includes a support structure 24 comprising a fingerless glove 38 and a fitting system 26 comprising, in one embodiment, an elastic band 42 sewn into the shell of the glove 38. The glove 38 may or may not be lined with cloth. A lining may be of any suitable material including flannel, cotton, polyester, blends of the foregoing materials, and the like. The outer shell 39 of the glove 38 is typically constructed of a strong resilient material such as nylon or other polymeric material. The nylon shell 39 of the glove 38 may terminate in a durable (e.g. leather) palm covering only the palm of the hand 40. In some environments, insulation or simply a shell may cover the back of the hand. Alternatively, the hand 40 may be completely uncovered. The glove 38 typically leaves at least the working portion of the fingers substantially completely uncovered for freedom of movement. The electrical resistance heaters 44 may be secured inside the cloth lining of the glove 38 so as to directly contact the skin covering the vascular surface location 34c, when the shell 39 of the glove 38 is disposed proximate the forearm of a user. The electrical resistance heaters 44 may be attached to the lining of the glove 38 by means of sewing but may be attached by any other suitable means or fasteners such as rivets, staples, adhesives, snaps, heat sealing, or the like.

In the depicted embodiment, the elastic band 42 serves to comfortably place the electrical resistance heaters 44 over vascular surface location 34c near the wrist of a user. The elastic band 42 urges the electrical resistance heaters 44 into complete engagement with the vascular surface location 34c to enable the conduction of heat through the user's skin and into the bloodstream. Other suitable fitting systems 26 may comprise hook-and-loop fasteners, buckles, straps, ties, strings, and the like.

As shown in FIG. 5, the batteries are contained in a battery pouch 46 attached to the anterior side of the fingerless glove 38. The battery pouch 46 includes a flap 48 that may be opened for emplacement and removal of the batteries within the battery pouch 46. The flap 48 is removably attached to the battery pouch 46 by a snap fastener 50. The battery pouch 46 may, for example, be disposed on the anterior or posterior side of the user's forearm in a location calculated to maximize the user's freedom of movement and comfort.

The circulation warmer 10 depicted in FIGS. 4 and 5, heats the blood that flows into the hand 40 thereby causing vasodilation (i.e. cause to increase in diameter) the arteries leading to the hand and the veins leading away from the hand. The hand and fingers are thus warmed, not by capture of body heat by an external covering, but by increased circulation and warmer internal blood. A small residual flow of heat from the electrical resistance heaters 44 through the skin by conduction to the exposed fingers also occurs.

Since the electrical resistance heaters 44 are disposed at vascular surface location 34c where relatively little motion occurs (e.g. proximate the forearm and wrist), the electrical resistance heaters 44 need not be flexible and, in fact, may be fairly rigid. Also, placement of the electrical resistance heaters 44 on the forearm and wrist permits the hand and fingers to remain uncovered and unobstructed for maintenance of dexterity and tactile sense therein. Many cold weather activities require, or are more easily performed when, the dexterity and tactile sense of the hands and finger are unimpeded by gloves, mittens or other coverings. For example, complete use of the fingers and hands is often desirable in activities conducted under cold environmental conditions such as construction, maintenance, hunting, fishing, and many other outside activities.

The heating elements are located away from the extremities where comparatively large relative motion is required. Thus, very substantial insulation may also be easily placed around the outside of the heating elements without obstructing motions of interest to a user. With the use of insulation around the electrical resistance heaters 44, substantially all the heat generated may be conducted into the bloodstream, thus increasing the efficiency of the overall energy use and transfer.

In another presently preferred embodiment of the circulation warmer depicted in FIGS. 4 and 5, the contact pads 20 be disposed alternatively over vascular surface locations 34b, 34d, or 34e, alone or in combination.

Figure 6:
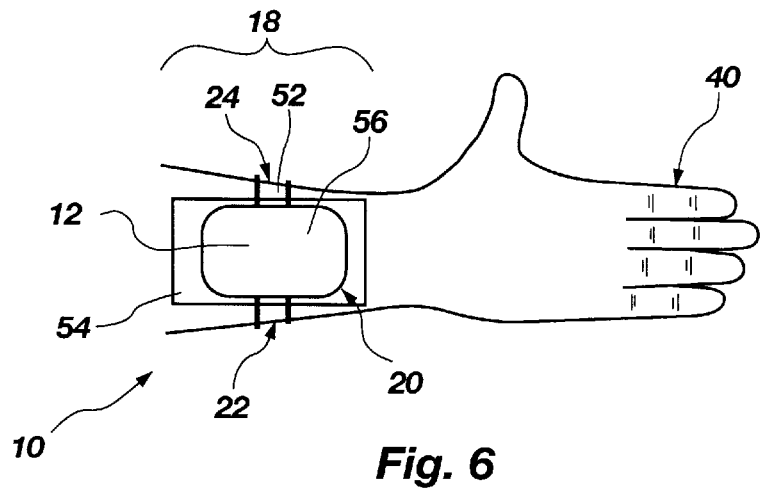
FIG. 6 is a perspective view of an alternative embodiment of the circulation warmer in accordance with the invention.

Referring to FIG. 6, an alternative embodiment of a circulation warmer 10 may include a vascular delivery system 18 in which the positioner 22 includes a support structure 24 comprising a securing strap 52 for securing the warmer 10 over the vascular surface location 34c. The securing strap 52 may include a fitting system 26 (not shown) that enables sizing of the securing strap 52 to fit the forearm of any user. The depicted embodiment also includes an insulation pad 54 for protecting the skin of a user and a pouch 56 for containing heat-producing chemical reactions or slowly burning combustible materials.

In the embodiment of FIG. 6, the combustion of comparatively slowly burning combustible materials or the reaction of a mixture of heat-producing chemicals in the pouch 56 may generate heat. The placement of the pouch 56 in complete contact with the vascular surface location 34c causes the heat to be conducted through the insulation pad 54 and through the skin of the user, as described hereinabove.

Figure 7:
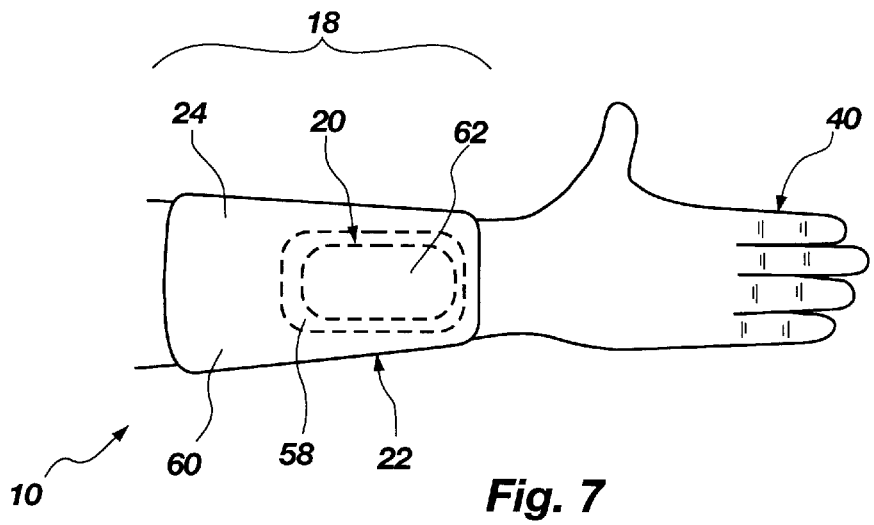
FIG. 7 is a perspective view of an alternative embodiment of the circulation warmer in accordance with the invention.

Referring to FIG. 7, another alternative embodiment of a circulation warmer 10 may include a vascular delivery system 18 in which the positioner 22 comprises a support structure 24 formed of a resilient material such as nylon surrounding an insulation wrap 60 disposed around the forearm of a user. In the embodiment of FIG. 7, a contact pad 20 may comprise a pouch 62 for containing a heat retaining solid and may be incorporated into the insulation wrap 60 so as enable the pouch 62 to be brought into complete contact with the vascular surface location 34c. Alternatively, as shown in the depicted embodiment, the vascular delivery system 18 may also include an insulation pad 58 disposed beneath the pouch 62 to protect the skin of a user by increasing the temperature gradient to mitigate the effects of excessive temperature produced by some heat-retaining solids that may be used in connection with the depicted embodiment.

In the embodiment of FIG. 7, a heat-retaining solid or thermal salt that has been pre-heated or chemically prepared may be placed inside the pouch 62. The placement of the pouch 62 into complete contact with the vascular surface location 34c causes the heat stored in the heat-retaining solid to be conducted through the insulation pad 58 and through the skin of the user, as described hereinabove.

Figure 8:
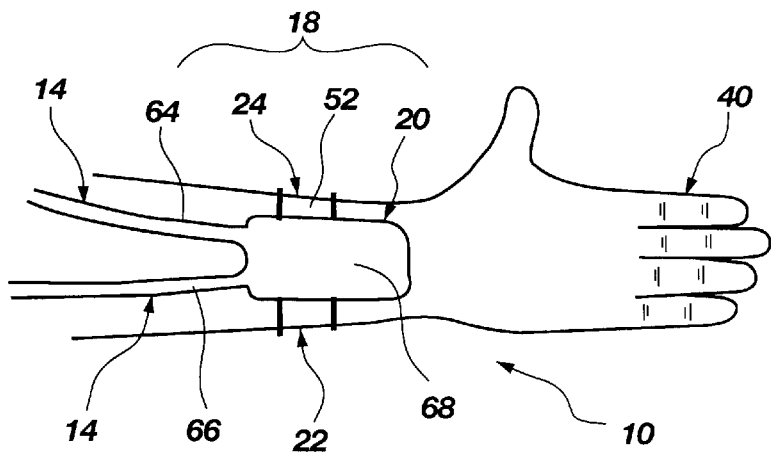
FIG. 8 is a perspective view of an alternative embodiment of the vascular delivery system of the circulation warmer in accordance with the invention.

Referring to FIG. 8, the vascular delivery system 18 of a fluid-based circulation warmer 10 may include a contact pad 20 to which warm fluid is supplied by a transfer path 14 comprising an inlet tube 64 and an outlet tube 66. The depicted embodiment includes a support structure 24 comprising a securing strap 52 similar to the securing strap 52 described in connection with the embodiment of FIG. 6. The contact pad 20 may comprise a fluid pouch 68 that is brought into complete contact with the vascular surface location 34c. In the embodiment of FIG. 8, heated fluid is circulated through the fluid pouch 68. Heat is conducted from the heated fluid circulating through the fluid pouch 68 through the skin and into the bloodstream of a user.

Figure 9:
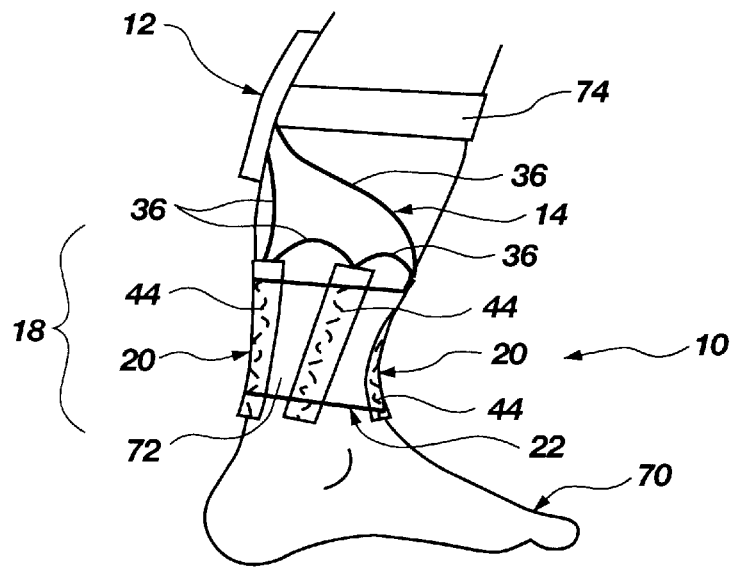
FIG. 9 is a posterior perspective view of an alternative embodiment of the circulation warmer in accordance with the invention.
Figure 10:
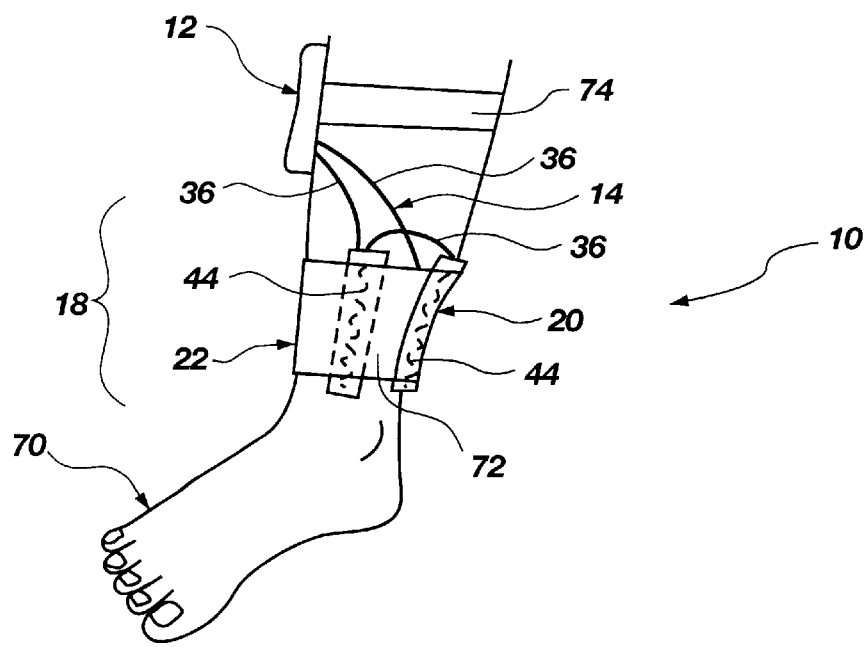
FIG. 10 is an anterior perspective view of the embodiment of the circulation warmer of FIG. 9 in accordance with the invention.

Referring to FIGS. 9 and 10, an alternative embodiment of the circulation warmer 10 may comprise an energy source 12, transfer paths 14, and a vascular delivery system 18 for use near the foot 70 of a user. In the depicted embodiment, the vascular delivery system 18 further comprises contact pads 20 and a positioner 22. In the depicted embodiment, the energy source 12 may comprise one or more batteries (not shown) for storing and providing electrical energy. The transfer paths 14 comprise electrical wires 36, and the contact pads 20 comprise electrical resistance heaters 44. The electrical resistance heaters 44 produce heat as electricity from the energy source 12 passes therethrough.

In the depicted embodiment, the positioner 22 of the vascular delivery system 18 comprises a flexible strap 72 to which the electrical resistance heaters 44 are sewn or attached by other suitable fasteners such as rivets, staples, adhesives, snaps, or the like. In the depicted embodiment, the flexible strap 72 serves to comfortably place the electrical resistance heaters 44 over vascular surface locations 34h, 34i, 34j and/or 34k near the ankle of a user. The flexible strap 72 urges the electrical resistance heaters 44 into complete engagement with the vascular surface locations 34 to enable the conduction of heat through the user's skin and into the bloodstream. The flexible strap 72 may be formed of an elastic material and may also be formed of any material suitable for maintaining the electrical resistance heaters 44 in comfortable engagement with the skin of a user near the ankle.

As shown in FIGS. 9 and 10, the energy source 12 may be suitably and comfortably secured to the leg of a user by a securing strap 74. The securing strap 74 may be adjustable to comfortably fit a variety of user leg sizes and shapes. The energy source may be secured to the leg of a user in any comfortable location that permits a user to have significant freedom of leg movement.

The circulation warmer 10 depicted in FIGS. 9 and 10, heats the blood that flows into the foot 70 thereby causing vasodilation (i.e. increase in diameter) of the arteries leading to the foot and the veins leading away from the foot. The foot and toes are thus warmed, not by an external covering capturing body heat, but by increased circulation of warmer internal blood. A small residual flow of heat from the electrical resistance heaters 44 through the skin by conduction to the foot and toes also occurs.

The electrical resistance heaters 44 are located away from those portions of extremities where comparatively small space for clearances and motion are available. Thus, very substantial insulation may be easily placed around the outside of the heating elements without obstructing motion of a user. With the use of insulation around the electrical resistance heaters 44, substantially all the heat generated may be conducted into the bloodstream, thus increasing the efficiency of the overall energy use and transfer.

Figure 11:
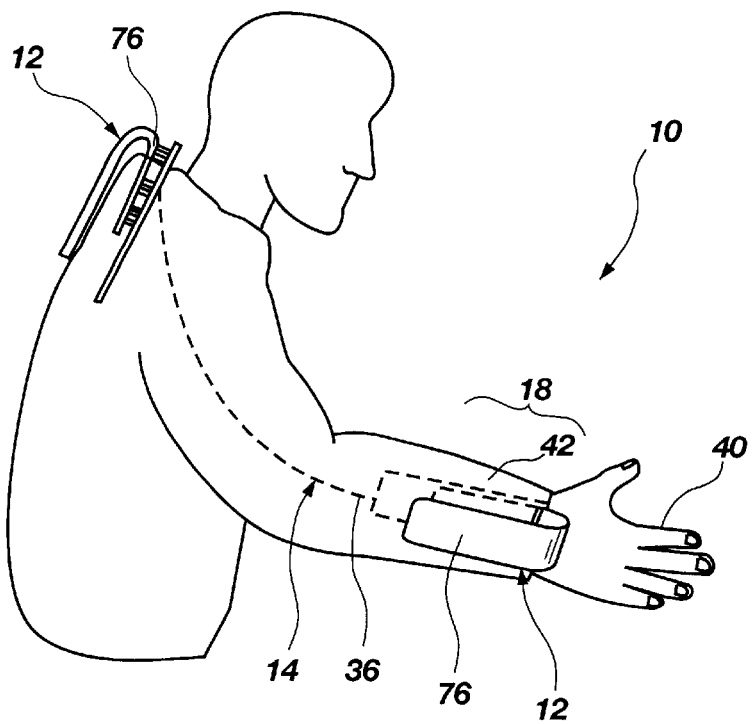
FIG. 11 is a perspective view of an alternative embodiment of an energy source for the circulation warmer of FIG. 4 in accordance with the invention.

Referring to FIG. 11, an energy source 12 for use with the circulation warmer 10 based on electrical energy of FIGS. 4 and 5 may comprise a thermoelectric converter 76. In the depicted embodiment, a thermoelectric converter 76 is placed near the base of user's neck or the torso, or another heat "source." Another thermoelectric converter 76 is placed near the wrist of a user. Thermoelectric converters 76 convert heat energy into DC electric current. As with other warmers 10 based on electricity, transfer paths 14 comprising electrical wires 36 connect the thermoelectric converters 76 to the vascular delivery system 18 of the circulation warmer 10. The vascular delivery system 18 of the embodiment depicted in FIG. 11 may be comprised of the same elements as the vascular delivery systems 18 of the embodiments of FIGS. 4, 5, 9, and 10.

Figure 12:
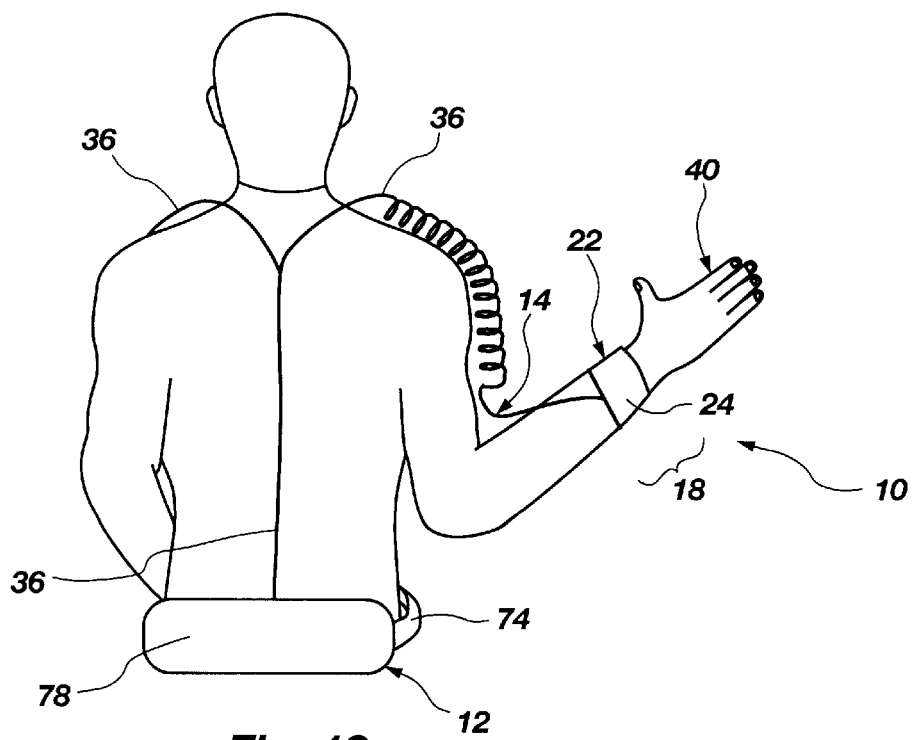
FIG. 12 is a perspective view of another alternative embodiment of an energy source of the circulation warmer of FIG. 4 in accordance with the invention.

Referring to FIG. 12, an alternative embodiment of the circulation warmer of FIGS. 4 and 5 may include an energy source 12 comprising a large battery pack 78 disposed about the waist of a user and attached thereto by a securing strap 74. The securing strap 74 may be adjustable fit users of a variety of sizes and shapes. In the depicted embodiment, the battery pack 78 is connected to the vascular delivery system 18 by transfer paths 14 comprising electrical wires 36. The electrical wires are preferably disposed along the spinal column and then across the shoulders and down the arms of a user to enable the user to enjoy maximum freedom of movement while wearing an apparatus 10 such as the depicted embodiment. Again, the vascular delivery system 18 of the embodiment depicted in FIG. 12 may be comprised of the same elements as the vascular delivery systems 18 of the embodiments of FIGS. 4, 5, 9, and 10 or may be comprised of other suitable elements that will maintain electrical resistance heaters 44 in complete contact with the vascular surface locations 34c.

Figure 13:
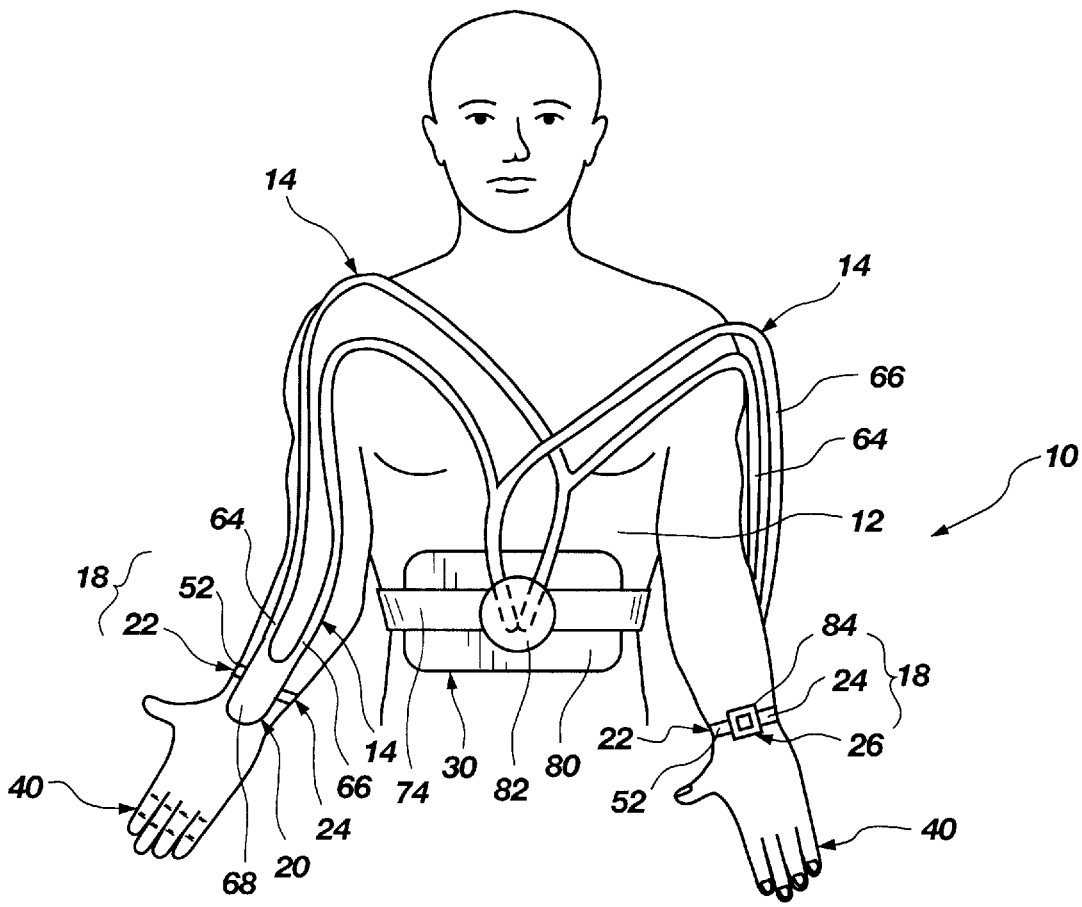
FIG. 13 is a perspective view of an alternative embodiment of the circulation warmer in accordance with the invention.

Referring to FIG. 13, a circulation warmer 10 may be based on transfer of heat into the bloodstream from circulation of fluid warmed by the natural heat generated within a user's body core. A circulation warmer 10 based on circulation of heated fluid may include transfer paths 14 comprising inlet tubes 64 and outlet tubes 66 for circulating fluid from a reservoir 30 to a vascular delivery system 18. The reservoir 30 may comprise a fluid warming pouch 80 disposed on or near the abdomen of a user. The warning pouch 80 may be secured to the body of a user by a securing strap 74, which may be adjustable to fit a variety of body sizes and shapes. A fluid pump 82 may be connected to the warming pouch 80. The fluid pump 82 may be employed to pump heated fluid from the warming pouch 80 through the inlet tubes 64 to the vascular delivery system 18.

The vascular delivery system 18 of the depicted embodiment may include the same elements as disclosed and described in connection with vascular delivery system 18 of FIG. 8. As shown in FIG. 13, the vascular delivery system 18 may include a contact pad 20 comprising a fluid pouch 68 secured to a vascular surface location 34c by a position 22 including a support structure 24 comprising a securing strap 52. The securing strap 52 maintains the fluid pouch 68 in complete contact with the vascular surface location 34c to enable the conduction of heat from the fluid circulating through the fluid pouch 68 through the skin and into the bloodstream of a user.

As depicted in FIG. 13, the positioner 22 also may include a fitting system 26 comprising a buckle 84 or adjustable fastener 84. The fastener 84 enables the adjustment of the securing strap 52 to comfortably fit a variety of sizes and shapes of forearms, while maintaining the fluid pouch 68 in intimate and complete contact with the vascular surface location 34c.

Figure 14:
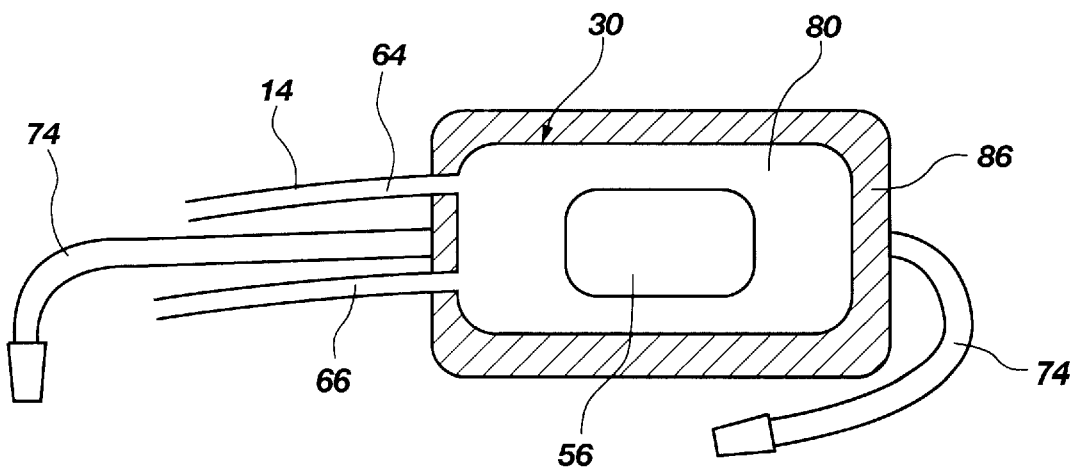
FIG. 14 is a cutaway top plan view of a reservoir and supplemental energy source for the circulation warmer of FIG. 13 in accordance with the invention.

FIG. 14 illustrates an alternate embodiment of the reservoir 30 of the fluid-based circulation warmer 10 depicted in FIG. 13. In the depicted embodiment, the reservoir 30 comprises a fluid warming pouch 80 having connected thereto a pouch 56 for containing heat-producing chemical reactions or slowly burning combustible materials. Heat produced by chemical reactions or material combustion in the pouch 56 may be conducted into the fluid circulating through the warming pouch 80 to supplement the heat provided by a user's body core heat and/or to prevent the excessive loss of consumption of body core heat.

An insulation pouch 86 may be disposed around the fluid warming pouch 80 and the pouch 56 to conserve and retain heat generated by the chemical reactions or combustion of materials within the pouch 56. Under extremely cold conditions, augmentation of the body heat produced by a user's body core with heat produced by a supplemental energy source 12, such as chemical reactions or slowly burning combustible materials, may be helpful. A supplemental energy source 12 may also be useful to prevent excessive lowering of body core temperature in extremely cold environments by drawing on a user's body core heat, as depicted in FIG. 13.

Figure 15:
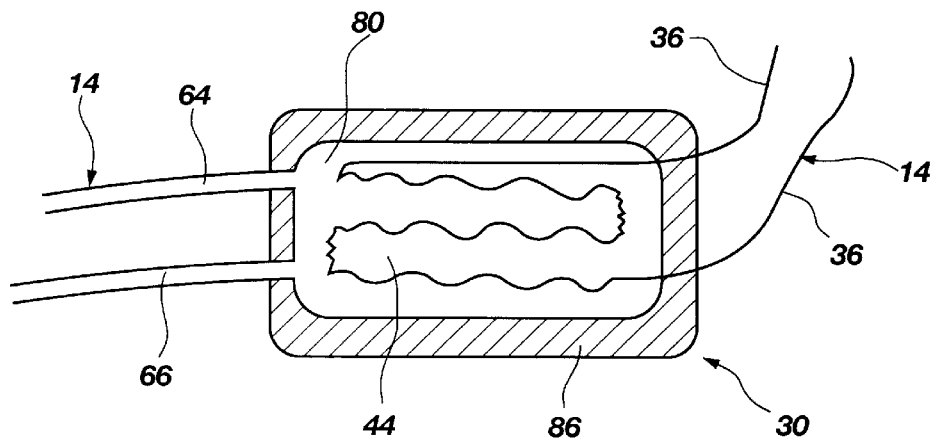
FIG. 15 is a cutaway top plan view of the reservoir and an alternative supplemental energy source of the circulation warmer of FIG. 13 in accordance with the invention.

FIG. 15 illustrates an alternate embodiment of the reservoir 30 and the supplemental energy source 12 of FIG. 14. The supplemental energy source 12 of FIG. 15 comprises electricity being circulated through electrical resistance heaters 44. The electrical resistance heaters 44 are connected to the fluid warming pouch 80, and heat produced by the electrical resistance heaters 44 is conducted into the fluid circulating through the fluid warming pouch 80. Similar to the embodiment of FIG. 14, an insulation pouch 86 may be disposed around the fluid warming pouch 80 to retain and conserve heat produced by the electrical resistance heaters 44.

Figure 16:
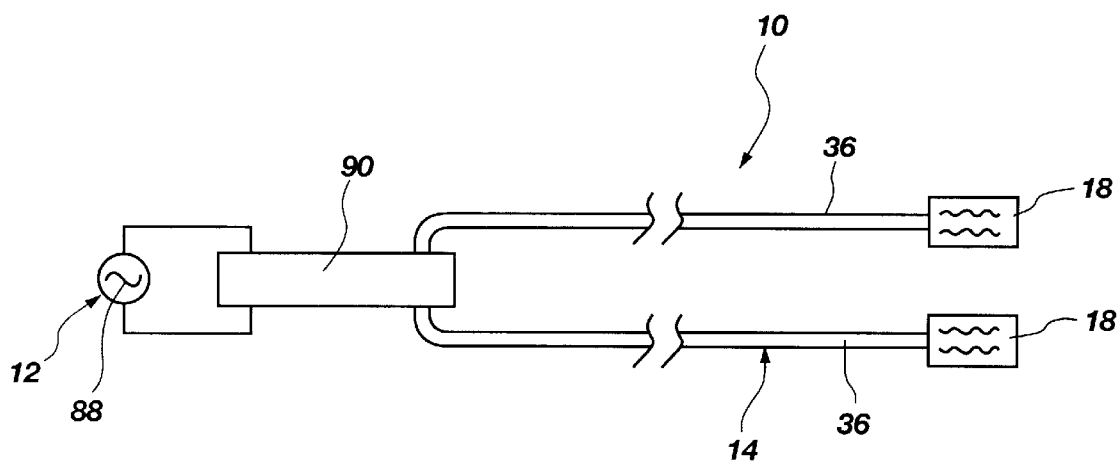
FIG. 16 is a schematic diagram of a circulation warmer having an electrical energy source in accordance with the invention.

Referring to FIG. 16, a circulation warmer 10 that employs conversion of electrical energy to heat may include an energy source 12 comprising an AC power source 88. The electricity produced by the AC power source 88 may be transmitted through an AC to DC converter 90 for transmission through transfer paths 14 comprising electrical wires 36 for conversion to heat by the vascular delivery system 18, as described in connection with FIGS. 4, 5, 9, and 10.

Figure 17:
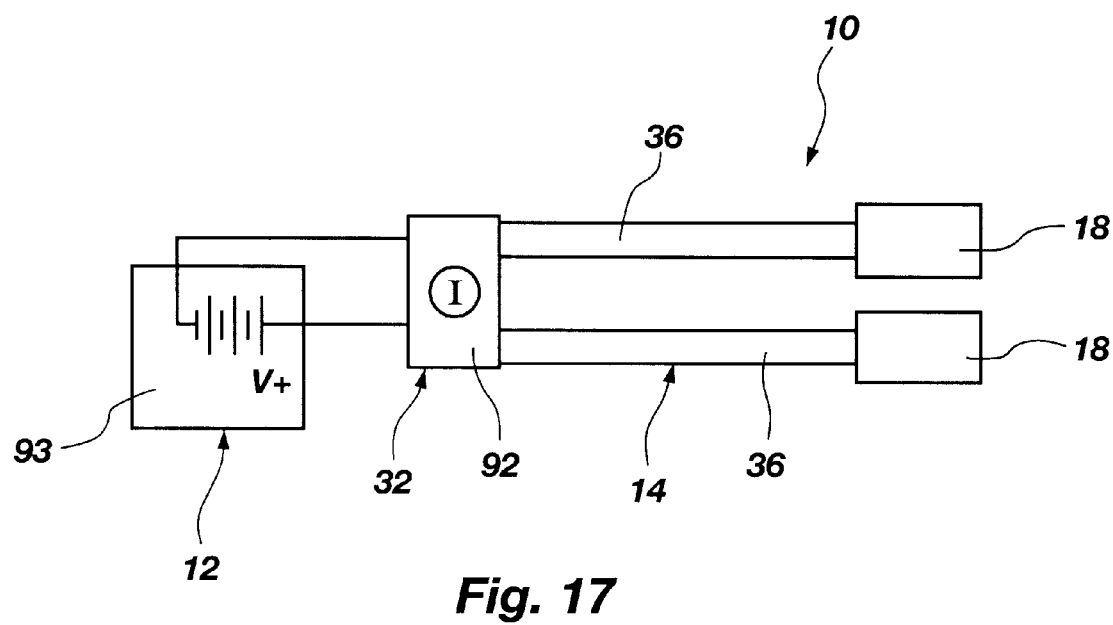
FIG. 17 is a schematic diagram of the circulation warmer of FIG. 16 having an alternative electrical energy source in accordance with the invention.

Referring to FIG. 17, a circulation warmer 10 that employs conversion of electrical energy to heat may include an energy source 12 comprising an DC power source 93. The electricity produced by the DC power source 93 may be transmitted through a controller 32 comprising a voltage amperage regulator 92 for controlling the amount of electrical energy that is transmitted through the wires 36 to the vascular delivery system 18 for conversion to heat.

Figure 18:
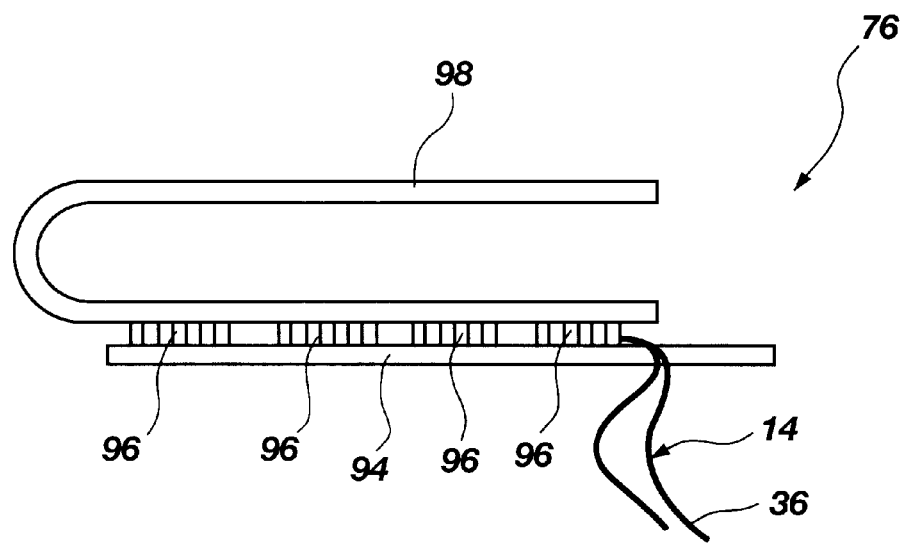
FIG. 18 is a close up elevation view of the alternative energy source of FIG. 11.

Referring to FIG. 18, a thermoelectric converter 76 may include a metal plate 94, converters 96, and a heat sink 98. The plate 94 maintains contact with the skin of a user to receive heat radiated from the user's skin. The heat sink 98 is exposed to the colder ambient air. The depicted thermoelectric converter 76 relies on the Seebeck Effect to convert the heat energy from a user's body into electrical energy for transmission of electricity through wires 36 for use as disclosed in connection with FIGS. 4, 5, 9, and 10.

Figure 19:
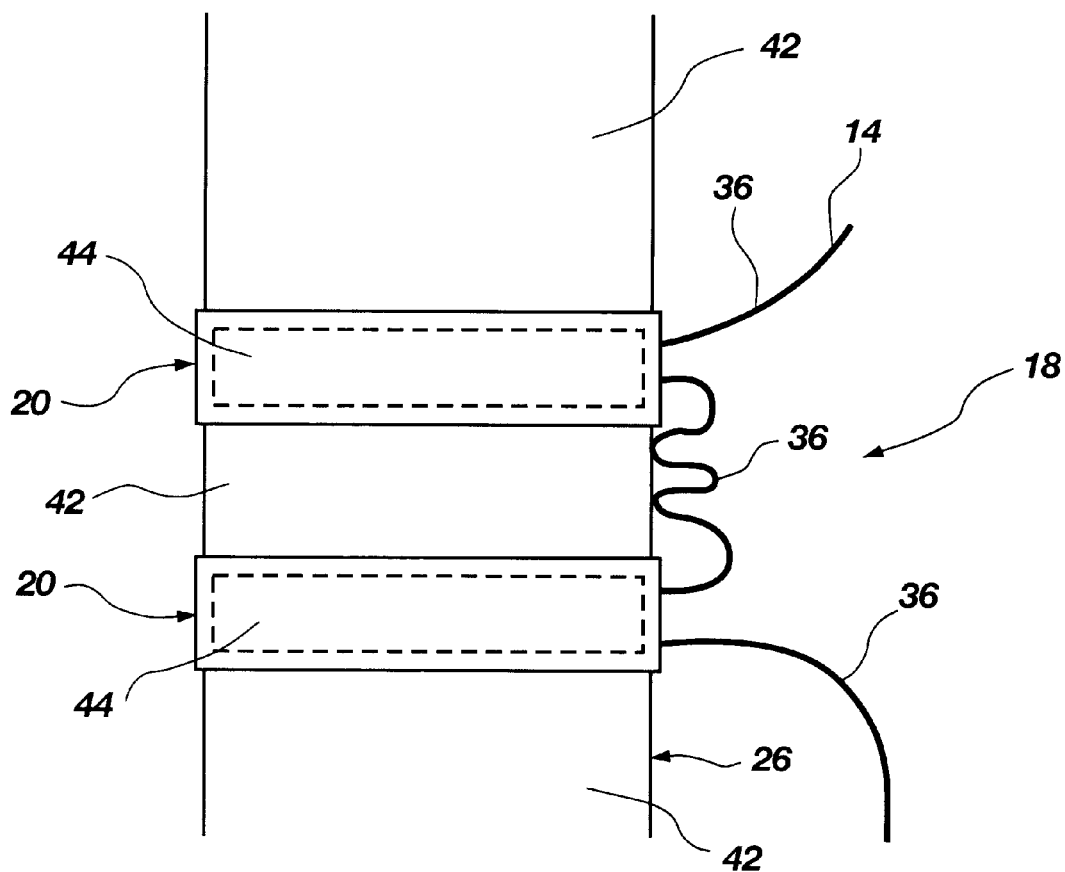
FIG. 19 is a top plan view of the vascular delivery system of FIG. 4 in accordance with the invention.

Referring to FIG. 19, the fitting system of the embodiment of FIGS. 4 and 5 may include electrical resistance heaters 44 sewn or attached to an elastic band 42. The elastic band 42 may be snugly fitted around the forearm and wrist of a user for complete contact of the electrical resistance heaters 44 with the vascular surface location 34c.

From the above discussion, it will be appreciated that the present invention provides a circulation warmer 10 for warming a body extremity while allowing the body extremity to be uncovered or sparsely covered so that dexterity and tactile sense in the body extremity are maximized. Unlike the prior art heated garments, the invention provides a circulation warmer 10 that requires no parts that are required to flex or bend such as the heating elements found in the prior art heated garments.

The invention also constitutes a circulation warmer that is simple and economical to manufacture, as well as being simple to maintain and use. The invention may be constructed largely from selected components, thereby minimizing specialized parts in its manufacture. Due to the relatively small size of the contact pads required for the invention, many embodiments of the invention function for relatively extended periods of time (3–8 hours) before extinguishing a relatively modest energy source such as a battery.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed and desired to be secured by United States Letters Patent is:

1. An apparatus for warming body extremity of a user under cold environment conditions without substantially degrading the dexterity and tactile sense of the body extremity while allowing the body extremity to be uncovered or sparely covered, the apparatus comprising:

an energy source suitable for generating and remotely distributing heat;

a vascular contact pad configured and positioned only at a vascular surface location on the user's skin to conduct said heat through the skin of a user and into the user's bloodstream in said vascular surface location;

a positioner attached to the contact pad for securing and effectively maintaining the contact pad in intimate and complete contact with said vascular surface location on the user's skin; and a transfer path connecting the energy source to the contact pad.

2. An apparatus for warming blood of a user as defined in claim 1, further comprising a controller configured to control the distribution of heat.

3. An apparatus for warming blood of a user as defined in claim 1, wherein distribution further comprises conversion from a first energy mode to heat.

4. An apparatus for warming blood of a user as defined in claim 1 wherein the apparatus further comprises an exchanger for exchanging energy from a first mode to a second mode.

5. An appars for warming blood of a user as defined in claim 4, wherein the first mode and the second mode are selected from the group consisting of conduction, convection, and radiation.

6. An apparatus for warming blood of a user as defined in claim 1, wherein the transfer path further comprises a line.

7. An apparatus for warming blood of a user as defined in claim 6, wherein the line is selected from the group consisting of an electrical line, a fluid line, and a heat transfer line.

8. An apparatus for warming blood of a user as defined in claim 1, wherein the contact pad is a vascular contact pad.

9. An apparatus for warming blood of a user as defined in claim 8, wherein the vascular contact pad is configured to conduct heat directly to the skin of a user proximate a subcutaneous vessel.

10. An apparatus for warming blood of a user as defined in claim 8, wherein the vascular contact pad further comprises a fluid conduit configured to convect heat from a working fluid to a contact surface.

11. A method for warming body extremity of a user under cold environment conditions without substantially degrading the dexterity and tactile sense of the body extremity while allowing the body extremity to be uncovered or sparely covered the method comprising:

placing a vascular contact pad only against a vascular surface location on a user's skin to be in thermally conducting relation thereto so that heat is conducted through said skin and into the user's bloodstream in said vascular surface location;

connecting the contact pad to an energy source configured to generate and remotely distribute heat;

transferring energy from the energy source toward the contact pad;

providing energy as beat through the contact pad;

conducting said heat from a contact surface of the contact pad to the skin; and conducting said heat from said skin into the bloodstream in said vascular surface location.

12. A method for warming blood of a user as defined in claim 11, further comprising securing the contact pad with a positioner.

13. A method for warming blood of a user as defined in claim 12, wherein the positioner is shaped and sized to conform to the body region proximate the vascular surface location.

14. A method for warming blood of a user as defined in claim 12, wherein the positioner includes a flexible material for providing comfortable fit to a user.

15. A method for warming blood of a user as defined in claim 12, wherein the positioner comprises elastic material for snugging the contact pad into complete contact with the vascular surface location.

16. A method for warming blood of a user as defined in claim 11, further comprising delivering energy to the contact pad.

17. A method for warming blood of a user as defined in claim 11, wherein the energy is electric current.

18. A method for warming blood of a user as defined in claim 11, wherein the energy is heated fluid.

19. A method for warming blood of a user as defined in claim 16, further comprising controlling the transfer of energy toward the contact pad.

20. A method for warming body extremity of a user under cold environment conditions without substantially degrading the dexterity and tactile sense of the body extremity while allowing the body extremity to be uncovered or sparely covered, the method comprising:

providing an energy source suitable for generating and remotely distributing heat;

providing a vascular contact pad configured and positioned only at a vascular surface location on the user's skin to conduct said heat through the skin of a user and into the user's bloodstream in said vascular surface location;

providing a positioner attached to the contact pad for securing and effectively maintaining the contact pad in intimate and complete contact with said vascular surface location on the user's skin;

providing a transfer path connecting the energy source to the contact pad; and transferring energy from the energy source toward the contact pad.

* * * * *

UNITED STATES PATENT AND TRADEMARK OFFICE
CERTIFICATE OF CORRECTION

PATENT NO.     : 6,268,595 B1
DATED          : July 31, 2001
INVENTOR(S)    : Jon Haehnel It is certified that error appears in the above-identified patent and that said Letters Patent is hereby corrected as shown below:

Title page,
At the title, inventor name misspelled, please delete "Haenel", and insert therefor -- Haehnel --.
Item [76], Inventor name misspelled throughout, please delete "Haenel", and insert therefor -- Haehnel --.
The address of the inventor is incorrect, please delete "340 Sugartop Rd., White River Junction, VT (US) 05045-9224, and insert therefore -- 287 Fairview Street, Fairlee, VT (US) 05045-9435 --.

ABSTRACT,
Line 7, after "surface location", please insert -- , --.

Column 14,
Line 31, after "claim 1", please insert -- , --.

Column 15,
Line 1, please delete "beat", and insert therefore -- heat --.

Signed and Sealed this

First Day of October, 2002

Attest:

JAMES E. ROGAN
Attesting Officer            Director of the United States Patent and Trademark Office